(12) United States Patent
Soukup et al.

(10) Patent No.: US 7,079,902 B2
(45) Date of Patent: Jul. 18, 2006

(54) SYSTEM FOR PROMOTING SELECTIVE TISSUE IN-GROWTH FOR AN IMPLANTABLE MEDICAL DEVICE

(75) Inventors: Thomas M. Soukup, Plymouth, MN (US); Stephen Sundquist, Minnetonka, MN (US); Roger Dahl, Andover, MN (US); Gregory A. Boser, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 10 days.

(21) Appl. No.: 10/671,103

(22) Filed: Sep. 25, 2003

(65) Prior Publication Data

US 2004/0059402 A1   Mar. 25, 2004

Related U.S. Application Data

(62) Division of application No. 09/827,103, filed on Apr. 5, 2001, now Pat. No. 6,704,604.

(51) Int. Cl.
*A61N 1/05* (2006.01)

(52) U.S. Cl. .................................. 607/116; 607/122
(58) Field of Classification Search ............. 607/1–2, 607/4–5, 115–129
See application file for complete search history.

(56) References Cited

U.S. PATENT DOCUMENTS

| | | | |
|---|---|---|---|
| 3,953,566 A | 4/1976 | Gore | 264/288 |
| 4,096,227 A | 6/1978 | Gore | 264/210 R |
| 4,161,952 A | 7/1979 | Kinney et al. | 128/786 |
| 4,187,390 A | 2/1980 | Gore | 174/102 R |
| 4,573,480 A | 3/1986 | Hirschberg | 128/784 |
| 4,934,049 A | 6/1990 | Kiekhafer et al. | 29/883 |
| 4,972,846 A | 11/1990 | Owens et al. | 128/784 |
| 4,985,296 A | 1/1991 | Mortimer, Jr. | 428/220 |
| 5,035,713 A | 7/1991 | Friis | 623/16 |
| 5,090,422 A | 2/1992 | Dahl et al. | 128/784 |
| 5,148,806 A | 9/1992 | Fukui et al. | 128/639 |
| 5,314,430 A | 5/1994 | Bardy | 607/5 |
| 5,358,516 A | 10/1994 | Myers et al. | 607/116 |
| 5,437,900 A | 8/1995 | Kuzowski | 428/36.1 |
| 5,462,781 A | 10/1995 | Zukowski | 428/36.1 |
| 5,466,252 A | 11/1995 | Soukup et al. | 607/116 |
| 5,609,622 A | 3/1997 | Soukup et al. | 607/122 |
| 5,626,561 A | 5/1997 | Butler et al. | 604/49 |
| 5,716,394 A | 2/1998 | Bruchman et al. | 623/1 |
| 5,782,898 A | 7/1998 | Dahl et al. | 607/119 |
| 5,833,664 A | 11/1998 | Seare, Jr. | 604/174 |
| 5,957,970 A | 9/1999 | Shoberg et al. | 607/722 |
| 6,058,332 A | 5/2000 | Dahl | 607/119 |
| 6,330,464 B1 | 12/2001 | Colvin, Jr. et al. | 600/316 |
| 6,406,420 B1 | 6/2002 | McCarthy et al. | 600/16 |
| 6,546,292 B1 | 4/2003 | Steinhaus et al. | 607/116 |

*Primary Examiner*—Robert E. Pezzuto
*Assistant Examiner*—Kristen Mullen
(74) *Attorney, Agent, or Firm*—Michael C. Soldner; Girma Wolde-Michael

(57) ABSTRACT

A system including an implantable defibrillation electrode includes a first layer of porous Polytetrafluoroethylene (PTFE) adjacent to at least one surface of the defibrillation electrode, the first layer of porous PTFE having a fibril length adapted to bleed gas away from the at least one surface of the defibrillation electrode, and a second layer of porous PTFE formed over the first layer, the second layer of porous PTFE having a fibril length adapted to prevent substantially all tissue in-growth.

17 Claims, 9 Drawing Sheets

SYSTEM FOR PROMOTING SELECTIVE TISSUE IN-GROWTH FOR AN IMPLANTABLE MEDICAL DEVICE

RELATED APPLICATIONS

This Application is a divisional of Ser. No. 09/827,103, now U.S. Pat. No. 6,704,604, filed Apr. 5, 2001.

FIELD OF THE INVENTION

The present invention relates generally to implantable medical devices; and more particular, relates to implantable devices that include an exterior structure to selectively promote tissue ingrowth.

BACKGROUND OF THE INVENTION

Transvenous cardioversion and defibrillation leads typically employ cardioversion or defibrillation electrodes taking the form of elongated metal coils. These coils may be applied to the exterior surface of the lead body, as disclosed in U.S. Pat. No. 4,934,049 issued to Kiekhafer et al.

One problem associated with defibrillation coils of the type discussed in the '049 patent involves the occurrence of tissue in-growth around the coil structure of the electrode. This is particularly true when the coil electrode is formed around the lead body so as to create an enlarged profile at the location of the coil as compared to the rest of the lead body. Tissue attachment that occurs proximal to the electrode structure makes it difficult to extract distal end of the lead, including the enlarged coil.

One way to reduce the problem of tissue in-growth involves providing defibrillation coils that are isodiametric with respect to the lead body. Such isodiametric electrode coils may be molded into the electrode body or the coils may be machined to provide a flush surface. This is described in U.S. Pat. No. 4,161,952, issued to Kinney et al. Similarly, U.S. Pat. No. 5,957,970 to Shoberg discloses an isodiametric defibrillation lead manufactured by removing a portion of an extruded tubular lead body in the region of the coil so that the electrode is flush with the surface of the lead. The 6944 Model lead commercially available from the Medtronic Corporation provides an isodiametric lead of this design.

Although isodiametric coil electrodes reduce problems associated with extracting an enlarged lead portion from ingrown tissue, other problems still exist related to ingrowth. For example, tissue commonly attaches around the coils of a defibrillation electrode, further increasing the difficulty associated with lead extraction.

Various methods have been attempted to overcome the problems associated with tissue in-growth around coil electrodes. One solution disclosed in the '049 patent referenced above involves injecting silicone rubber into the spaces between the individual coils of an electrode. The resulting thin coating of silicone rubber surrounding the exterior of the coils of electrode minimizes tissue in-growth between the filars of the coils, while leaving a portion of the coils exposed to deliver electrical stimulation to a patient.

Another approach to preventing tissue in-growth is disclosed in U.S. Pat. No. 5,090,422, which describes the use of a biocompatible porous materials such as woven, porous polyurethane and porous polytetrafluoroethylene that may be used to cover an electrode surface. The material is insulative when dry, but becomes conductive when bodily fluids penetrate the pores of the material. The porous covering is of adequately small pore size and fibril length to preclude substantial tissue in-growth.

Yet another method of preventing tissue in-growth is disclosed in U.S. Pat. No. 5,609,622, which describes coating a lead with a porous Polytetrafluoroethylene (PTFE) layer such as may be formed of expanded PTFE (e-PTFE), and which has a pore size of less than 10 microns or smaller so that the pore size is very small, and tissue in-growth is prevented.

While the foregoing approaches are directed to preventing tissue in-growth, it may be noted that some controlled tissue attachment to a lead body or electrode may actually be beneficial in stabilizing the lead, and allowing the electrode to maintain a position at a desired implant site. For example, in leads carrying defibrillation electrodes, a change in the coil placement may increase the defibrillation thresholds. Similarly, in pace/sense applications, a shift in electrode position may alter the pacing threshold and affect capture. Promoting tissue growth for stabilizing prosthesis and other implanted structures has been disclosed in the prior art. For example, U.S. Pat. No. 5,035,713 discusses use of a re-entrant biocompatible material such as polyethylene, polyethylene teraphthalate, polypropylene, polysulfone, polylactic acid and polydioxanone to promote selective tissue in-growth to stabilize an implanted structure. Similarly, U.S. Pat. No. 5,833,664 discusses promoting tissue attachment to intrabody prosthetic devices, such as catheters, to effect improved stability of the prosthesis/tissue opening site interface.

Yet a further concern associated with the use of medical electrical leads, and in particular, the use of leads carrying coiled electrode structures, involves the possibility of a coil causing abrasion to an adjacent lead structures. For example, a coiled electrode adapted for use in the right atrium may lie in close proximity to a second lead carrying an electrode placed in the right ventricle. The coiled electrode may contact the second lead, creating abrasions in the external lead surface so that an internal conductor comes in contact with body fluids. This condition may ultimately result in lead failure. Also, in applications in which leads are positioned within relatively smaller vasculature structures, such as in coronary veins, lead-to-lead contact, or lead-to-tissue contact can be exacerbated, thus increasing the likelihood of abrasion.

Therefore, what is needed is an improved lead structure that minimizes the potential for the abrasion of adjacent structures. The lead ideally promotes selective, controlled tissue attachment to stabilize lead placement, while preventing tissue ingrowth that would prevent lead extraction.

SUMMARY OF THE INVENTION

The present invention provides an improved system and method of selectively promoting tissue in-growth on, or adjacent to, an implantable medical device (IMD). In one embodiment of the invention, a first portion of porous PTFE is provided adjacent to at least a first surface of the IMD. The porous PTFE, which may be an expandable PTFE (e-PTFE), has a pore size that is small enough to prevent substantially all tissue ingrowth. For example, the pore size may be 10 microns or less. This first portion of PTFE is adjacent at one or more selected locations to a second portion of porous PTFE. This second portion of PTFE has a pore size adapted to promote tissue in-growth. For example, the pore size of this second portion may be 20 to 50 microns. In this manner, tissue in-growth will only occur at the first surface of the IMD in the vicinity of the second portions of PTFE. At other areas of the first surface of the IMD, all tissue ingrowth will be substantially prevented.

In another embodiment of the invention, the inventive system includes a removable member that is adapted to be adjacent to at least one surface of the IMD. The removable member is formed of a first portion, or layer, of porous PTFE to substantially prevent all tissue in-growth, and one or more second portions, or layers, of porous PTFE that are provided to promote tissue in-growth in selected locations. The removable member may take the form of a sleeve, as may be adapted to slide over a portion of a lead. This sleeve may be adapted to remain in the body of a patient during a lead extraction process so that a replacement lead may be advanced within the sleeve. Because the sleeve is adapted for preventing tissue in-growth in the lead itself, the lead extraction process is greatly simplified.

According to one embodiment of the invention, each of the PTFE layers are formed of porous PTFE tubing having a thickness of 50 microns or less, and preferably less than 25 microns. The tubing may be heat-shrinkable such that it conforms to a specific surface of an electrode or other implantable medical device upon the application of heat. In yet another embodiment of the invention, the layers of porous PTFE may be formed of a tape that may be applied to the surface of the implantable medical device. In still a further embodiment of the invention, the two layers are provided by a single composite structure that has a more porous material exposed on a first surface adapted to be located adjacent tissue, and a less porous, more dense material on a second surface adapted to be situated adjacent the electrode. This type of composite structure may be formed by first creating a coating of e-PTFE having a unified density. One surface of the composite structure may then be altered to be more porous by selectably removing fibrils from this surface. Alternatively, this structure may be formed using a co-extrusion process to create the layers with different pore sizes.

According to one manner of using the current invention, a lead having at least one coil electrode is coated with an inner layer of porous PTFE such as expanded-PTFE (e-PTFE) to prevent tissue in-growth. This inner layer is surrounded by a more porous PTFE layer having a pore size selected to promote tissue in-growth. The tissue ingrowth promoted by the pore size of the outer layer is controlled such that the coil electrode is stabilized at a desired implant site by the tissue attached to this layer. Tissue is prevented from adhering to any part of the coil structure itself by the inner layer.

The current invention may be adapted for selectively promoting tissue in-growth in subcutaneous electrode arrays, and in any other type of implantable lead or electrode system. In addition to promoting tissue in-growth to stabilize the location of an implantable medical device, the current system also prevents lead abrasion cause by electrode coils rubbing against adjacent lead structures when multiple leads are in close communication with one another within a patient's vascular system.

Other aspects of the invention will become apparent to those skilled in the art from the description of the invention and the accompanying drawings.

DETAILED DESCRIPTIONS OF THE DRAWINGS

Figure 1:
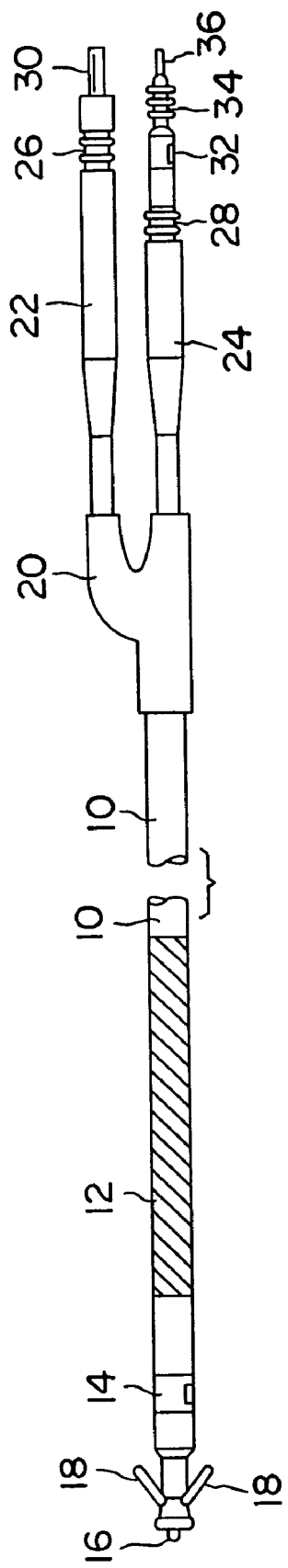
FIG. 1 is a plan view of a defibrillation lead of the type in which the present invention may usefully be practiced.

FIG. 1 is a plan view of a defibrillation lead of the type in which the present invention may usefully be practiced. It will be understood the lead of FIG. 1 is merely exemplary, and the present invention may also be usefully practiced in the context of any other implantable medical electrical leads or implantable medical devices generally. The lead of FIG. 1 is provided with an elongated insulative lead body 10, preferably fabricated of silicone rubber, polyurethane or other biocompatible, compressible elastomer. The distal end of the lead carries an elongated defibrillation electrode 12, a ring electrode 14, and a tip electrode 16. A fixation mechanism such as tines 18 may be provided to maintain electrode 16 in contact with body tissue. Electrodes 12, 14, and 16 may correspond to any conventionally available pacing and defibrillation electrodes.

The proximal end of the lead carries a connector assembly that includes a molded lead bifurcation sleeve 20. This bifurcation sleeve joins the lead body 10 to two different connectors at the lead proximal end. The first connector is a bipolar, in-line assembly 24, generally corresponding to the IS-1 connector standard for pacing leads. This connector 24 is provided with a first and second set of sealing rings 28 and 34, and connector pin 36. Connector pin 36 may be coupled to tip electrode 16 via an internal conductor, whereas the connector ring may be coupled in a similar manner to ring electrode 14. The second connector, which may correspond to a standard such as DF-1, is provided to couple connector pin 36 to defibrillation electrode 12.

Although the lead of FIG. 1 is shown with a single defibrillation electrode 12, the lead may further include more than one defibrillation electrode by locating additional electrodes sequentially along the length of the lead body.

Figure 2:
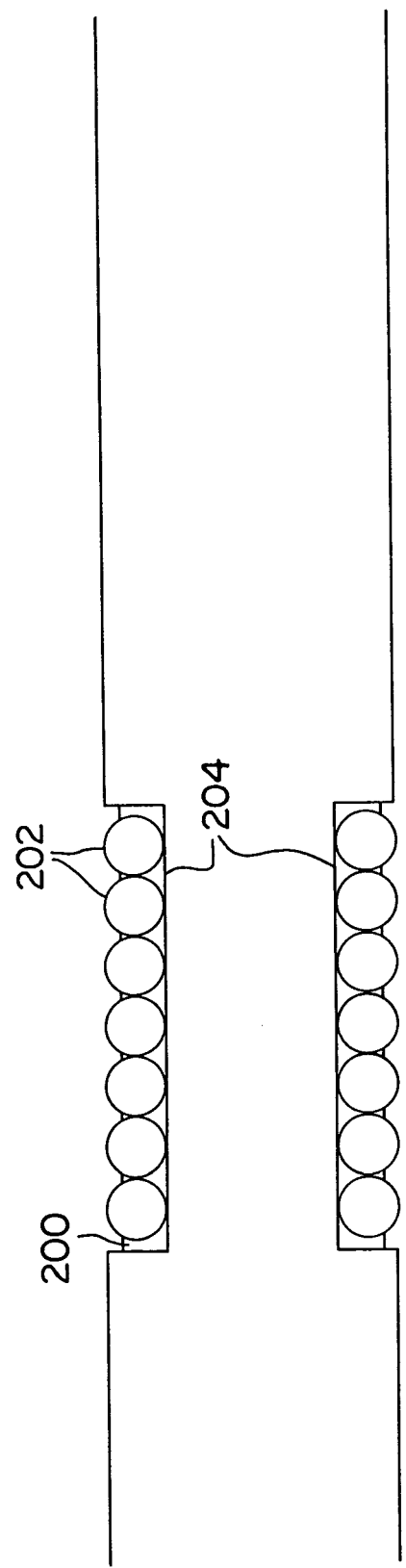
FIG. 2 is an exploded side cutaway view of a defibrillation coil including silicone backfill to prevent tissue in-growth in a manner known in the art.

FIG. 2 is an exploded side cutaway view of a defibrillation coil including silicone backfill to prevent tissue in-growth in a manner known in the art. As discussed above, prior art leads utilize an injected silicone rubber layer 200 applied between the spaces of the individual electrode coils 202 to prohibit tissue attachment around these coils. These coils may be located within a grooved region 204 of the lead 206 to provide a structure that is isodiametric, as shown in FIG. 2. Alternatively, the coils may be located around the outer diameter of the lead such that the coil has a diameter that is larger than the diameter of the remainder of the lead.

The injection of silicone around the defibrillation coils involves a process that must be closely controlled. If too much silicone is injected around the coils, the conductive capability of the defibrillation electrode may be comprised. If too little silicone is injected, tissue in-growth may not be prevented, making lead extraction difficult or impossible.

Figure 3:
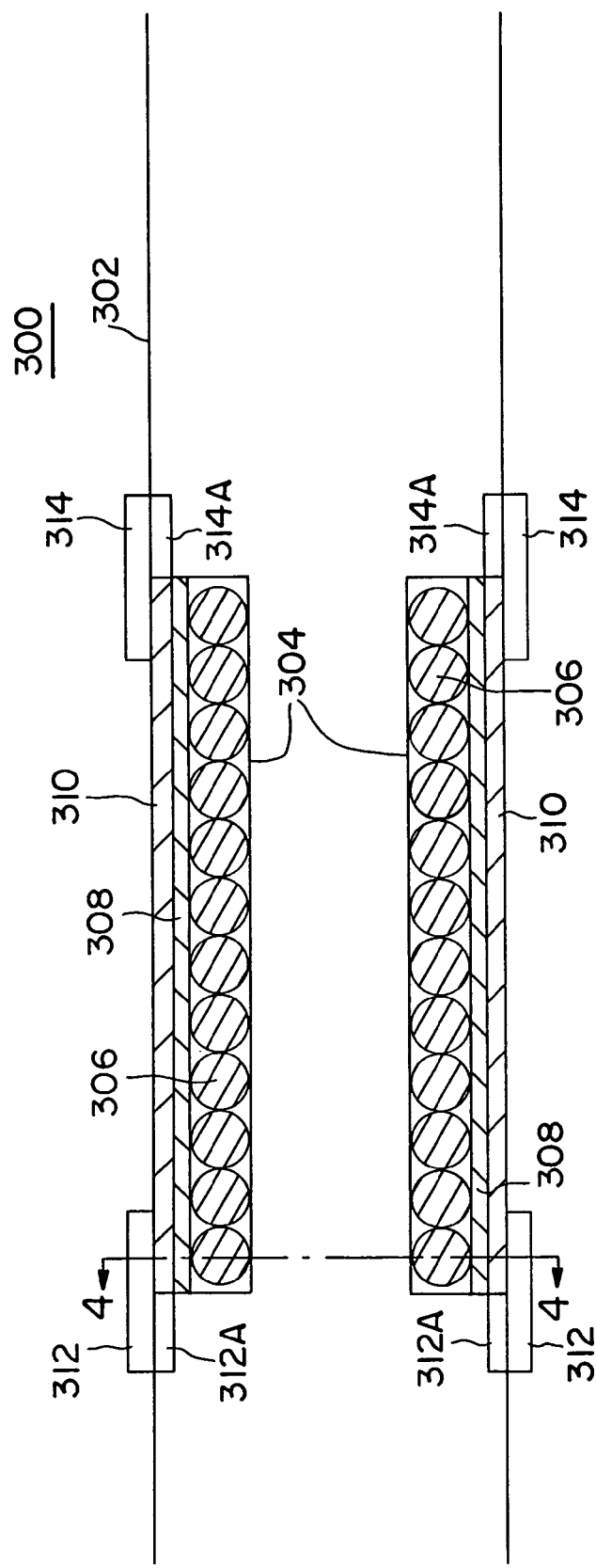
FIG. 3 is a side cutaway view of one embodiment of a lead according to the current invention.

FIG. 3 is a side cutaway view of one embodiment of a lead 300 utilizing the current invention. The lead body 302 includes a grooved region 304 that retains defibrillation coil 306 which may be of any construction known in the art. Adjacent defibrillation coil is a layer 308 of a porous PTFE having a pore size that is adequately small to preclude tissue in-growth. A material particularly suited for this purpose is expanded PTFE (e-PTFE), which is known to be chemically inert and biocompatible. In one embodiment, the pore size of the porous PTFE material of layer 308 is less than 10 microns. In a preferred embodiment, the pore size is between 3 and 5 microns to prevent substantially all tissue growth associated with coil 306.

As noted above, the porous PTFE used in the construction of the inventive lead is preferably porous expanded PTFE (e-PTFE) having a microstructure of nodes interconnected by fibrils. Porous expanded PTFE may be manufactured according to the processes disclosed in U.S. Pat. Nos. 4,187,390, 3,953,566, 5,609,622, 4,096,227, 4,187,390, 4,985,296 and 5,148,806, all incorporated herein by reference. The porous PTFE may contain a carbon filler used for the surface of the conductive portion of the electrode. As is known in the art, porous PTFE may be specified by pore size, which, in turn, is generally described as a function of the fibril length of the material. The fibril length of porous expanded PTFE is measured as taught by U.S. Pat. No. 4,972,846.

Returning now to FIG. 3, an outer layer 310 of porous PTFE such as e-PTFE surrounds inner layer 308. The material of layer 310 has a pore size (fibril length) adapted to selectively promote tissue in-growth. In one embodiment, the pore size of the material included in layer 310 is between 20 and 50 microns. The tissue in-growth promoted by the pore size of layer 310 is controlled such that the defibrillation coil is stabilized at a desired implant site by the tissue attached to this layer. However, tissue is prevented from adhering to any part of the coil structure itself by inner layer 308 so that tissue in-growth around the coil does not prohibit lead extraction. Because both layers 310 and 308 are porous, body fluids that are retained within the pores allows these layers to conduct electricity when the lead is implanted.

According to one aspect of the invention, layer 310 may be treated, or infused, with of drugs to minimize thrombosis as well as to reduce the threat of infection.

In one embodiment, layers 308 and 310 are cut from tubing commercially-available from the Zeus Corporation of Orangeburg, S.C. In this embodiment, each of the layers may be very thin, having a thickness of 50 microns or less, and preferably less than 25 microns.

The tubing of both layers may be sized to fit grooved region 304. Layers 308 and 310 may be held in place using any type of biocompatible adhesive such as silicone adhesive. Alternatively, the adhesive may be a thermoplastic adhesive such as a dispersion of water and fluorinated ethylene propylene in the form of a particulate and a surfactant. A layer of non-conductive polymeric adhesive produces good adhesion with little additional electrical resistance. Alternatively, conductive fillers such as carbon black may be added to this dispersion in order to make it electrically conductive. This dispersion, both with, or without conductive fillers, may be used to adhere the electrically conductive polymeric material of the electrode surface to the underlying coil 306.

Layers 308 and 310 may be bonded together using an ultrasonic welding process, as is known in the art. In another embodiment tubing may be sized larger than grooved region 304 such that edges of layers 308 and 310 extend over regions 312A and 314A of the lead body.

According to one construction of a lead employing the current invention, sleeves 312 and 314, which may be formed of silicone or other biocompatible material, may be applied over the edges of the layers 308 and 310 and held in place by an adhesive to further secure these structures. Alternatively, a tubing structure, including heat-shrinkable tubing, may be used for this purpose. Bonding of sleeves 312 and 314 to the lead body may be enhanced by etching regions 312A and 314A of the lead body 302 using a plasma or corona etching process, or by using a chemical surface modification process such as is commercially performed by the Zeus Corporation. This creates a surface that more readily adheres to adjacent materials, allowing a superior bond to form between the lead body surface and the sleeves 312 and 314. Yet another approach to improving the bond involves utilizing an ultrasonic welding process to bond the sleeves to the surface of lead body 302.

It may be noted that the body of lead 302 may be of any conventional lead construction known in the art in the manner discussed above. For example, the exterior of lead may be formed of a silicone, a polyurethane, or a non-porous or dense PTFE. These materials do not promote tissue in-growth in the manner discussed above with respect to porous PTFE. For this reason, only limited tissue in-growth occurs along the primary portion of the lead body, with more substantial in-growth being selectively promoted only where an additional degree of stability is desired, as at the electrode.

Figure 4:
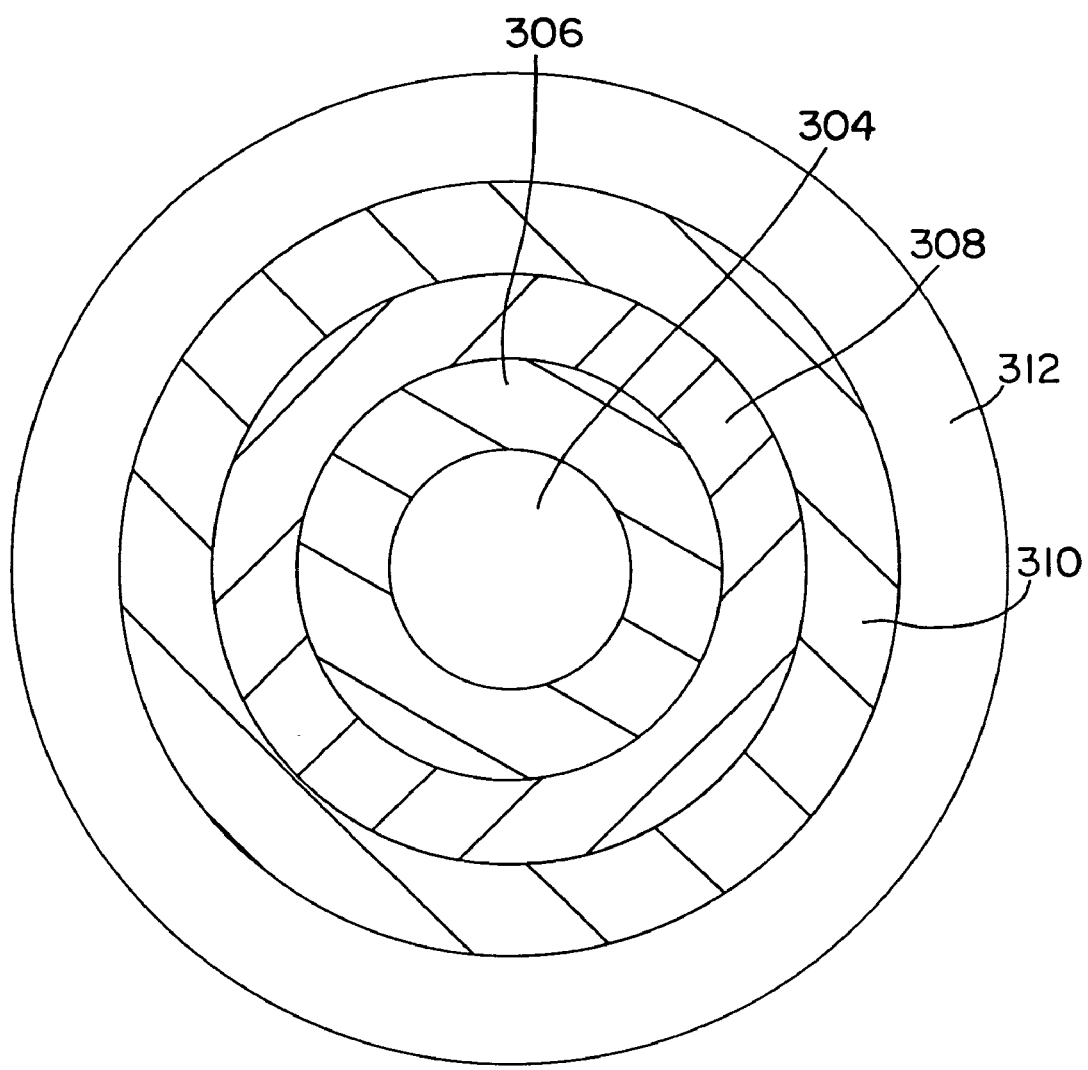
FIG. 4 is a cross-sectional view of the lead of FIG. 3 at line 4—4.

FIG. 4 is a cross-sectional view of the lead of FIG. 3 at line 4—4. This view shows grooved region 304 surrounded by coil 306. The inner and outer porous PTFE layers 308 and 310, respectively, encircle the coil 306. In one embodiment, sleeve 312 may further surround layer 308.

Figure 5:
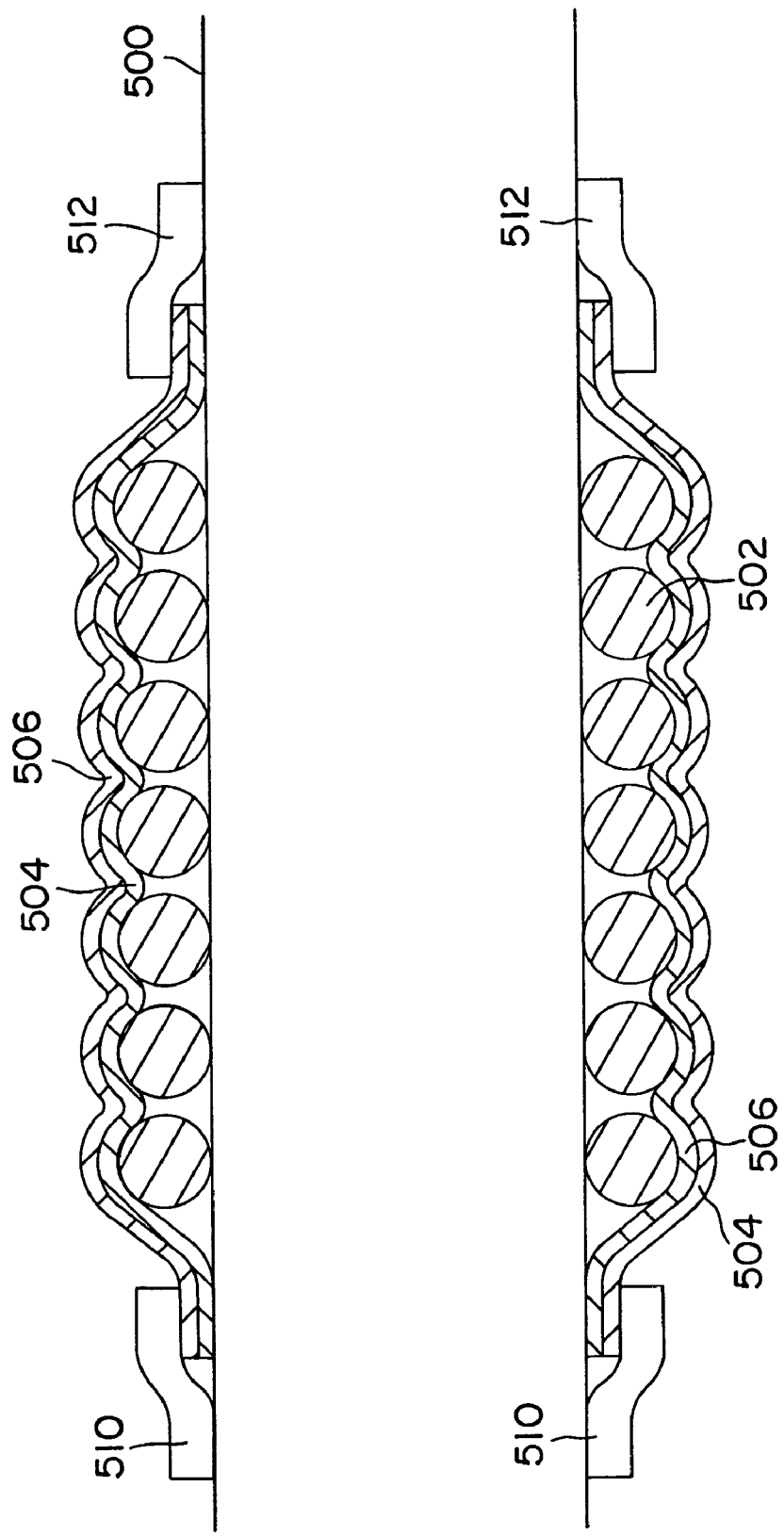
FIG. 5 is side cutaway view of an alternative embodiment of a lead configured according to the current invention.

FIG. 5 is an alternative embodiment of a lead according to the current invention. In this embodiment, lead body 500 does not include a grooved portion. Instead, coil 502 encircles the outer diameter of the lead body. According to one method of manufacturing this embodiment, tubing may be employed to form porous PTFE layers 504 and 506. Inner layer 504 is formed of a porous PTFE tubing having a pore size of less than 10 microns, whereas the tubing of layer 506 is formed of porous PTFE having a pore size of between 20 and 50 microns in the manner discussed above. Such tubing is commercially available from the Zeus Corporation. The tubing may be heat-shrinkable, making use of an adhesive unnecessary. Alternatively, a medical grade adhesive may be utilized to affix layers 504 and 506 to the lead. The lead may further include sleeves 510 and 512 encircling the edges of the porous PTFE layers 504 and 506 to aid in attaching these layers to the lead body 500.

In yet another embodiment of lead 302 or 502, the layers of porous PTFE may be formed of a tape that may be applied to the surface of the electrical conductor. For example, a porous PTFE may be formed into a thin sheet. A layer of continuous or discontinuous thermoplastic adhesive may be applied to one side of the sheet, and the material may then be cut to form tape. The tape forming the inner layer is wrapped about the conductor wire surface with the adhesive side of the composite contacting the conductor. In one embodiment, the conductor wire surface is helically wrapped with the tape, and is then heated to a temperature above the melt point of the thermoplastic adhesive to cause effective bonding of the composite tape to the conductor surface. This process may be repeated with a second tape formed using a less-dense PTFE.

The above-described embodiments contemplate the use of two individual layers of porous PTFE to selectively control tissue in-growth. An inner layer prevents substantially all in-growth, while the surrounding, outer layer selectively promotes in-growth. In one embodiment of the invention, the two layers are combined into a composite structure that has a more porous material exposed on a first surface adapted to be located adjacent tissue, and a less porous, more dense material on a second surface adapted to be situated adjacent the electrode. For example, a heat-shrinkable, tubular structure that is adapted to be positioned around defibrillation electrode 12 may have an outer surface formed of a more porous e-PTFE, with the inner surface coated with a less porous e-PTFE. Such a structure may be formed initially of a dense e-PTFE. The outer surface may then be altered to be more porous by selectably removing fibrils from the outer surface using the techniques described in U.S. Pat. No. 5,462,781 incorporated herein by reference.

Figure 6:
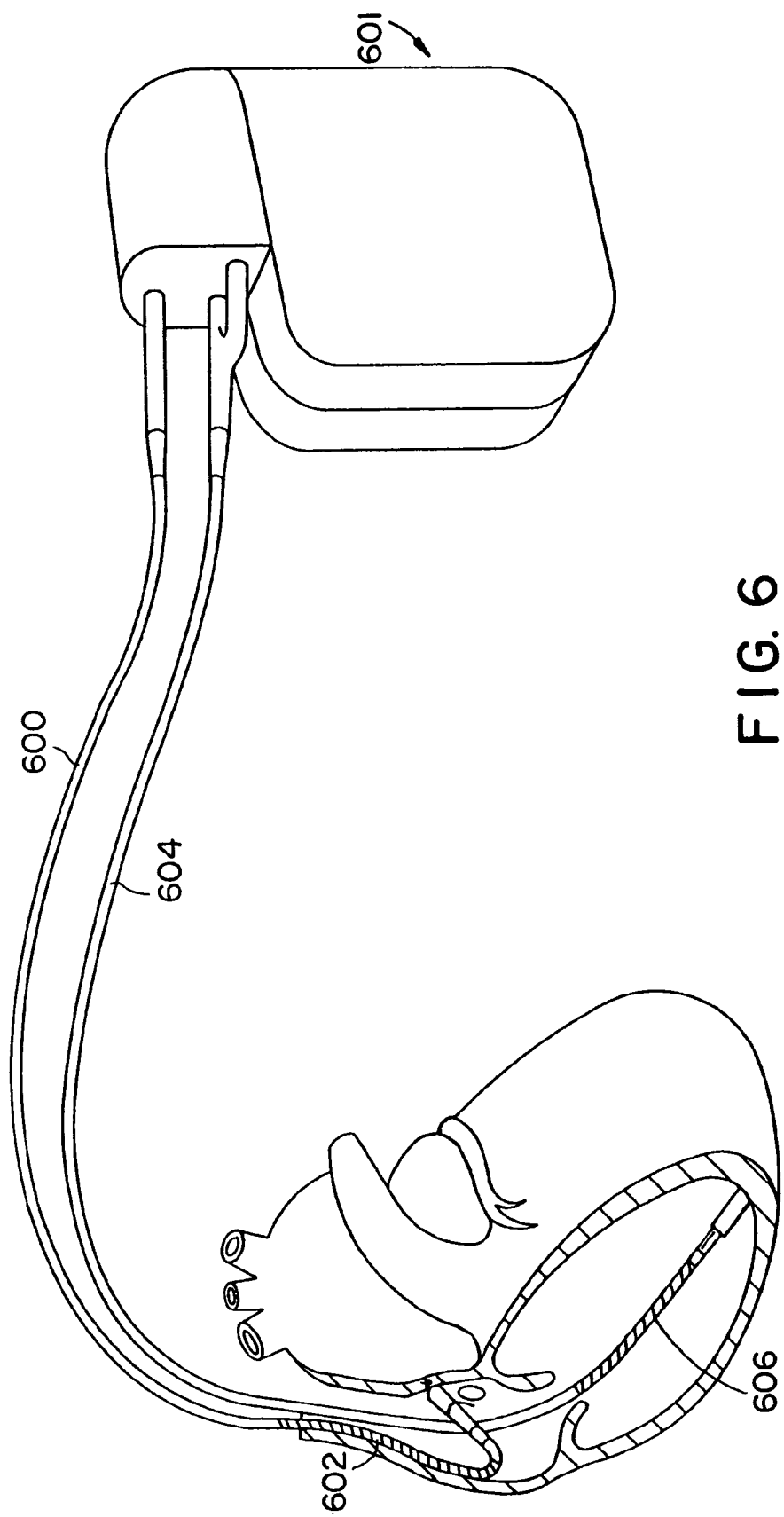
FIG. 6 is a diagram depicting two defibrillation leads placed within a human heart, and illustrates use of the current invention to prevent lead abrasion.

FIG. 6 is a diagram depicting two defibrillation leads placed within a human heart, and illustrates yet another advantage of the current invention. A first lead 600 carries a defibrillation electrode 602 that is located within the right atrium, wherein a second lead 604 carries an electrode 606 positioned in the right ventricle. Both leads are shown coupled to implantable pulse generator 601. Electrode 602 is in close proximity to the body of lead 604 such that abrasion of the lead outer surface by the coil 602 is likely. This abrasion may be minimized using the current inventive lead, which provides multiple layers of the porous PTFE material over the electrode. These layers form a lubricious, non-abrasive surface over electrode 602 such that wear on adjacent lead structures may be substantially eliminated. This is important for chronically-implanted leads adapted for long-term use.

Figure 7:
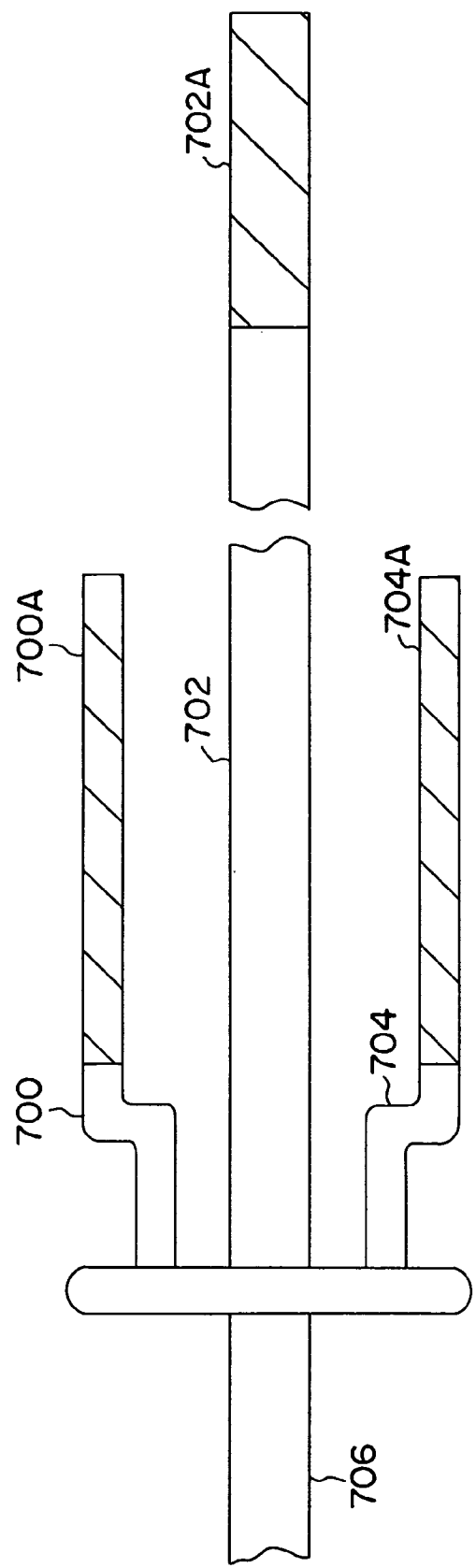
FIG. 7 illustrates a subcutaneous defibrillation electrode array that is particularly adapted for use with the current invention.

FIG. 7 illustrates a subcutaneous defibrillation electrode array that is particularly adapted for use with the current invention. Such an electrode array is designed to be positioned under a patient's skin, and may be used in conjunction with the system and method described in U.S. Pat. No. 5,314,430. The electrode array includes multiple elongated lead structures 700, 702, and 704 that each couples to an implantable pulse generator using a common connector 706. Although the exemplary electrode array shows three lead structures, more than three may be provided. Each of the lead structures carries a respective defibrillation electrode shown as electrodes 700A through 704A. According to the configuration of FIG. 7, common connector 706 and the electrodes of shorter leads 700 and 704 may be implanted under the skin of a patient's chest, for example. Longer lead 702 may be tunneled under the skin around the patient's side, and extending under the skin of the patient's back. This positioning of the electrodes both on the chest and back of the patient allows a lower defibrillation threshold to be achieved. However, the configuration also promotes lead abrasion. For example, the electrode coils on leads 700 and 704 may abrade the surface of lead 702. The current invention may be readily adapted for use with a subcutaneous defibrillation electrode array of the type shown in FIG. 7 so that abrasion is reduced.

Variations and modifications to the present invention may be possible given the above disclosure. For example, a composite structure comprising a first dense layer of porous PTFE surrounded by a second, less dense, layer of porous PTFE may be positioned adjacent to an outer surface of any implantable medical device, and is not limited to use with electrodes carried on leads. For example, the enclosure (can) of an implantable medical device may employ the current invention system to promote tissue in-growth over a portion of the can, if desired. Alternatively, predetermined portions of the lead body itself may employ the inventive system and method to selectively promote tissue in-growth.

According to another manner of practicing the current invention, the various layers of PTFE may be staggered such that only a portion of the first, porous layer of PTFE is coated by an outer layer of less dense PTFE. In this manner, tissue in-growth is only selectively promoted at predetermined areas of the device, while being entirely absent at other areas of the device. For example, a medical lead may be coated with a layer of more dense e-PTFE over the entire length of the lead. The lead may then-be coated with an additional outer layer formed of a less dense material over only selected portions of the lead to allow selective tissue in-growth in only certain areas, such as adjacent to an electrode to stabilize electrode positioning. This enables lead extraction to be accomplished with less tissue damage.

According to yet another aspect of the invention, a sleeve having two layers of porous PTFE according to the current invention may be provided to encase a medical device. The sleeve may be formed of an inner layer of a porous PTFE having a pore size adapted to prevent substantially all tissue in-growth. An outer layer formed of the less porous PTFE in the manner discussed above may be provided over the entire surface, or only over predetermined portions, of the inner layer to selectively promote tissue in-growth. The sleeve may be positioned over the implantable medical device prior to implant. After implant, tissue in-growth occurs at the predetermined portions of the sleeve wherein the more porous PTFE material resides. No tissue attaches to the medical device itself. Therefore, the medical device may be readily replaced. For example, a lead may be withdrawn from the sleeve and a new lead inserted into the sleeve without disrupting the in-grown tissue, greatly simplifying the lead extraction process. Moreover, the stability of the implanted medical device is enhanced by the existence of the in-grown tissue and the sleeve. It may be noted that because the sleeve is porous, current is conducted through the sleeve when the pores are filled with fluid. Therefore, a lead inserted into a sleeve and implanted within a patient may deliver electrical stimulation to the patient through the PTFE layers.

Figure 8:
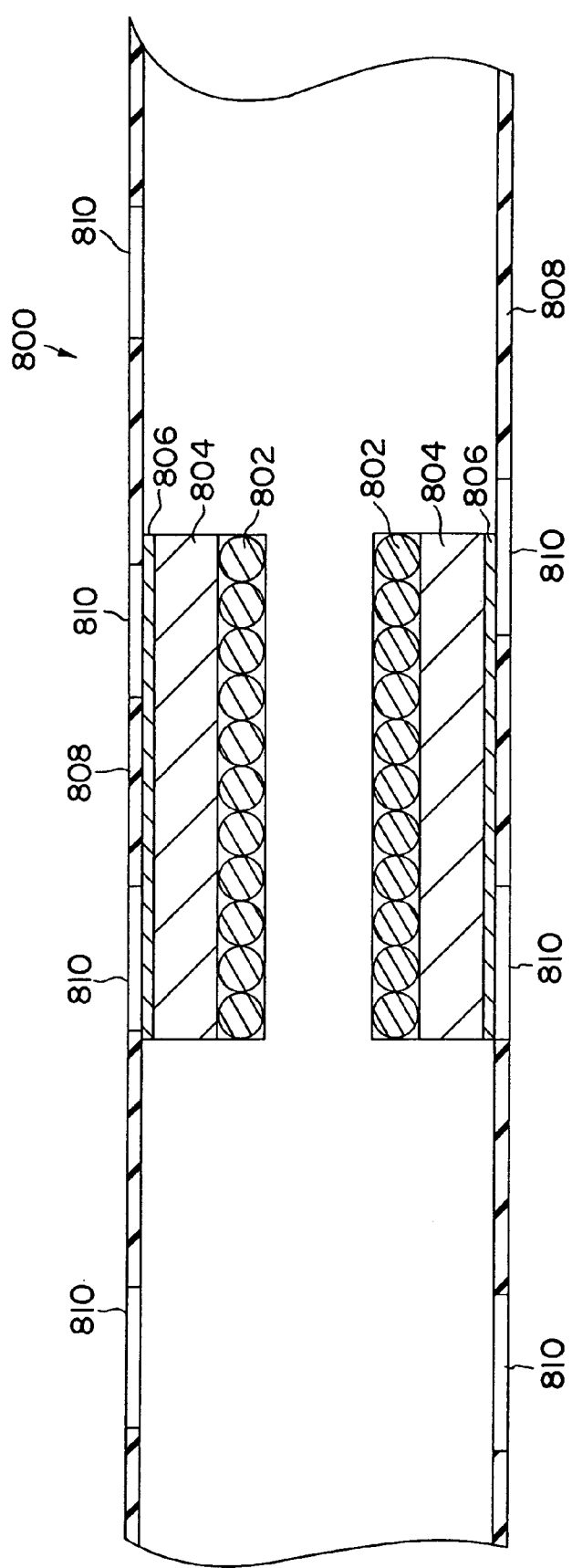
FIG. 8 is a partially cutaway side view of a lead including a defibriflation coil illustrating another embodiment of the current invention.

FIG. 8 is a partially cutaway side view of a lead 800 including a defibrillation coil 802 illustrating another embodiment of the current invention. In this embodiment, defibrillation coil is in contact with a first layer 804 of e-PTFE that is very porous, having a pore size which may range between 50 and 100 microns. In one embodiment, this first layer 804 may be 50 microns or more thick. Because of the very porous nature of this first layer, the first layer is able to absorb gas such as oxygen that is created by electrolysis during the delivery of electrical stimulation to the body. In other words, the porous layer bleeds the gas created during the delivery of a cardioversion/defibrillation shock from the surface of the electrode 802. This is important because applicants have shown that the build-up of gas around an electrode increases the effective impedance of the surrounding area, decreasing the current delivered during the shock pulses. This could affect shock efficacy. Providing the very porous layer prevents this increase of impedance from occurring.

The very porous first layer 804 may be coated with a second layer 806 of porous material having a pore size that substantially prevents all tissue in-growth in the manner discussed above. Layer 806 has a thickness which may be relatively small in comparison to layer 804. For example, the pore size of this layer may be 10 microns or less, with a layer thickness that may be 10 microns or less. Providing a second layer that is relatively thin reduces overall lead dimensions.

The inventive lead of FIG. 8 may, but need not, also include yet a third layer 808 of biocompatible material. This third layer 808 may include predetermined portions 810 of porous material such as e-PTFE having a pore size to selectively promote tissue in-growth in a manner discussed above. For example, the pore size may range between 20 and 50 microns. This third layer 808 therefore serves to maintain lead stability while not promoting in-growth to the extent that would hamper lead extraction. In one embodiment, this layer is as thin as possible, with a thickness of 50 microns or less, to reduce overall lead size.

The lead of FIG. 8 may be constructed using any of the methods and materials, and may further include any of the aspects, of the inventive leads discussed above.

Figure 9:
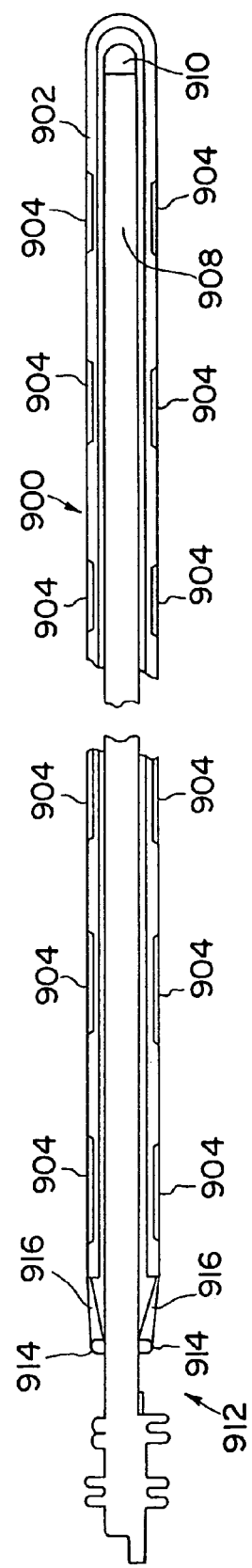
FIG. 9 is a side cutaway view of a lead inserted in a sleeve formed in accordance with the current invention.

FIG. 9 is a side cutaway view of a lead inserted in a sleeve formed in accordance with the current invention. Sleeve 900 includes an inner layer 902 of porous PTFE having a very small pore size to prevent substantially all tissue in-growth. An outer layer of PTFE may then be provided having a larger pore size. This outer layer may be formed over the inner layer 902 at selected locations 904 in the manner shown in FIG. 9, or over the entire sleeve. In one embodiment, the selected locations 904 are created by selectively removing fibrils from the more dense inner layer 902 in the manner discussed above. In another embodiment, cutaway regions are formed in the inner layer 902 into which a less dense PTFE material is inlaid and affixed with medical grade, electrically-conductive, adhesive.

FIG. 9 further illustrates a lead 908 inserted into sleeve 900. Lead may have one or more electrodes such as distal tip electrode 910 which may provide electrical stimulation to a body through the sleeve when the sleeve pores are filled with body fluid. The lead could also carry any of the many physiological sensors known in the art for monitoring physiological signals. In one embodiment, the proximal end of lead 912 includes fastening means such as small ring members 914 for fastening the sleeve to the lead as with surgical suture material 916, for example. Any other fastening means could be used for this purpose. Fastening means may be readily detached prior to the lead extraction procedure. In another embodiment, sleeve 900 is sized to only cover the lead distal end portion. It will be understood the sleeve length could be varied in any manner desired.

The sleeve of FIG. 9 may, in one embodiment, include an additional inner layer adapted to be positioned adjacent the lead formed of a porous PTFE having a pore size adapted to bleed gas away from the surface of the lead in the manner described above. If desired, this sleeve may include only the additional inner layer and the more dense layer 902, while omitting the less-dense layers 904 that are adapted to selectively promote tissue in-growth.

As noted above, although FIG. 9 illustrates use of a sleeve with a lead, such a sleeve may be adapted for use with any medical device adapted for implantation within a body. All such variations and modifications are intended to be within the scope of the invention claimed by this letters patent.

What is claimed is:

1. A system including an implantable defibrillation electrode, comprising:
    a first layer of porous Polytetrafluoroethylene (PTFE) adjacent to at least one surface of the defibrillation electrode, the first layer of porous PTFE having a fibril length adapted to bleed gas away from the at least one surface of the defibrillation electrode;
    a second layer of porous PTFE formed over the first layer, the second layer of porous PTFE having a fibril length adapted to prevent substantially all tissue in-growth; and
    a third layer of porous PTFE adjacent to at least a portion of the second layer, the third layer having a fibril length adapted to selectively promote tissue in-growth.

2. The system of claim 1, wherein the first layer of porous PTFE is an expanded PTFE (e-PTFE).

3. The system of claim 1, wherein the second layer of porous PTFE is an expanded PTFE (e-PTFE).

4. The system of claim 1, wherein the first layer of porous PTFE includes pores each having a pore size of greater than or equal to 50 microns.

5. The system of claim 4, wherein the pores of the first layer of porous PTFE each have a pore size between 50 and 100 microns.

6. The system of claim 1, wherein the second layer of porous PTFE includes pores each having a pore size of less than or equal to 10 microns.

7. The system of claim 1, wherein the first layer is formed of tubing.

8. The system of claim 1, wherein the first layer is formed of tape.

9. The system of claim 1, wherein the third layer includes pores each having a pore size between 20 and 50 microns.

10. The system of claim 1, wherein the second layer is formed of tubing.

11. The system of claim 1, wherein the second layer is formed of tape.

12. The system of claim 1, wherein the first layer of porous PTFE has a thickness greater than or equal to 50 microns.

13. The system of claim 1, wherein the second layer of porous PTFE has a thickness less than or equal to 10 microns.

14. The system of claim 1, wherein the third layer of porous PTFE is an expanded PTFE (e-PTFE).

15. The system of claim 1, wherein a portion of the third layer is formed over the second layer.

16. The system of claim 1, wherein a portion of the third layer is longitudinally offset from the second layer.

17. A system including an implantable defibrillation electrode, comprising:
    a first layer of porous Polytetrafluoroethylene (PTFE) adjacent to at least one surface of the defibrillation electrode, the first layer of porous PTFE having a fibril length adapted to bleed gas away from the at least one surface of the defibrillation electrode;
    a second layer of porous PTFE formed over the first layer, the second layer of porous PTFE having a fibril length adapted to prevent substantially all tissue in-growth; and
    a third layer of porous PTFE adjacent to at least a portion of the second layer, the third layer having a fibril length adapted to selectively promote tissue in-growth, the third layer of porous PTFE has a thickness less than or equal to 50 microns.

* * * * *